US009622667B2

(12) United States Patent
Hirahara

(10) Patent No.: US 9,622,667 B2
(45) Date of Patent: Apr. 18, 2017

(54) BLOOD PRESSURE MEASURING APPARATUS AND BLOOD PRESSURE MEASURING METHOD

(71) Applicant: NIHON KOHDEN CORPORATION, Tokyo (JP)

(72) Inventor: Hideaki Hirahara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/824,572

(22) Filed: Aug. 12, 2015

(65) Prior Publication Data

US 2015/0342473 A1    Dec. 3, 2015

Related U.S. Application Data

(62) Division of application No. 13/110,968, filed on May 19, 2011, now Pat. No. 9,119,537.

(30) Foreign Application Priority Data

May 21, 2010  (JP) ................................ 2010-116978

(51) Int. Cl.
*A61B 5/02* (2006.01)
*A61B 5/021* (2006.01)
(Continued)

(52) U.S. Cl.
CPC .......... *A61B 5/02116* (2013.01); *A61B 5/022* (2013.01); *A61B 5/02225* (2013.01); *A61B 5/7278* (2013.01)

(58) Field of Classification Search
None
See application file for complete search history.

(56) References Cited

U.S. PATENT DOCUMENTS 4,074,711 A    2/1978  Link et al.
4,360,029 A *  11/1982 Ramsey, III .................. 600/494
(Continued)

FOREIGN PATENT DOCUMENTS

CN    1105224 A    7/1995
CN    1270793 A    10/2000
(Continued)

OTHER PUBLICATIONS

European Search Report, dated Sep. 12, 2011, issued in Application No. 11166825.7.
(Continued)

*Primary Examiner* — Navin Natnithithadha
*Assistant Examiner* — Michael R Bloch
(74) *Attorney, Agent, or Firm* — Sughrue Mion, PLLC

(57) ABSTRACT

A blood pressure measuring apparatus which measures a blood pressure in a step of gradually changing a cuff pressure adapted to press an artery, includes: a pulse wave detecting unit; a pulse wave interval measuring unit; a waveform information storing unit; a change trend calculating unit; a waveform information comparing unit; and a determining unit which, when first two of the pulse waves, which are successively detected at different cuff pressures, satisfy a predetermined condition: that a magnitude relationship between the amplitudes of the first two of the pulse waves is consistent with the change trend of the first two of the pulse waves; that the pulse wave interval between the first two of the pulse waves is within a predetermined range; and that the waveform information of the first two of the pulse waves approximately coincide with each other, determines that the amplitude of latter one of the first two of the pulse waves is to be used for calculating the blood pressure value.

3 Claims, 7 Drawing Sheets

(51) Int. Cl.
  *A61B 5/00* (2006.01)
  *A61B 5/022* (2006.01)

(56) References Cited

U.S. PATENT DOCUMENTS

| | | |
|---|---|---|
| 5,522,395 A | 6/1996 | Shirasaki et al. |
| 5,623,933 A | 4/1997 | Amano et al. |
| 5,653,241 A | 8/1997 | Harada et al. |
| 2002/0026121 A1 | 2/2002 | Kan |
| 2004/0077958 A1 | 4/2004 | Kato et al. |

FOREIGN PATENT DOCUMENTS

| | | |
|---|---|---|
| JP | 3057892 B2 | 7/2000 |
| JP | 3972144 B2 | 9/2007 |

OTHER PUBLICATIONS

Office Action dated Sep. 24, 2013 issued by the State Intellectual Property Office of the People's Republic of China in counterpart Chinese Patent Application No. 201110132443.2.

* cited by examiner

BLOOD PRESSURE MEASURING APPARATUS AND BLOOD PRESSURE MEASURING METHOD

CROSS-REFERENCE TO RELATED PATENT APPLICATION

This application is a Divisional application of U.S. application Ser. No. 13/110,968, filed on May 19, 2011, in the United States Patent and Trademark Office, which claims priority from Japanese Patent Application No. 2010-116978, filed on May 21, 2010, in the Japan Patent Office, the disclosures of which are incorporated herein by reference in their entireties.

BACKGROUND OF THE INVENTION

The present invention relates to a blood pressure measuring apparatus and a blood pressure measuring method.

From the viewpoint of reducing a burden on the subject, it is desired to shorten the measuring time in the blood pressure measurement which is performed by pressing an artery by a cuff. Usually, the time for measuring the blood pressure depends largely on the step of, after the pressing of an artery, gradually reducing the cuff pressure. In the blood pressure measurement using the oscillometric method, a pulse wave is detected from an artery while the cuff pressure is gradually reduced, and hence there is a possibility that the pulse wave is affected by disturbance noises (hereinafter, referred to as "artifacts") caused by a body motion or the like. In the related-art blood pressure measuring apparatus disclosed in U.S. Pat. No. 4,360,029, when, with respect to a specific cuff pressure, two successive pulse waves exhibit an approximately same waveform, the two pulse waves are used in calculation of the blood pressure value, thereby preventing the value from being affected by artifacts.

In the related-art blood pressure measuring apparatus disclosed in U.S. Pat. No. 4,360,029, even when pulse waves are not affected by artifacts, however, at least two pulse waves are always required with respect to a specific cuff pressure. This causes a problem in that a long time period is required for measurement.

SUMMARY

It is therefore an object of the invention to provide a blood pressure measuring apparatus and a blood pressure measuring method in which the time period for measuring the blood pressure when an artery is pressed by a cuff can be shortened.

In order to achieve the object, according to the invention, there is provided a blood pressure measuring apparatus which measures a blood pressure in a step of gradually changing a cuff pressure adapted to press an artery, the blood pressure measuring apparatus comprising: a pulse wave detecting unit which detects pulse waves of the artery; a pulse wave interval measuring unit which measures a pulse wave interval between two of the pulse waves that are successively detected; a waveform information storing unit which stores waveform information of the pulse waves, the cuff pressure at time when the pulse waves are detected, and the pulse wave interval; a change trend calculating unit which calculates a change trend of amplitudes of the pulse waves; a waveform information comparing unit which compares the waveform information of two of the pulse waves that are successively detected; and a determining unit which, when first two of the pulse waves, which are successively detected at different cuff pressures, satisfy a predetermined condition: that a magnitude relationship between the amplitudes is consistent with the change trend; that the pulse wave interval is within a predetermined range; and that the waveform information approximately coincide with each other, determines that the amplitude of latter one of the first two of the pulse waves is to be used for calculating the blood pressure value.

In a case where the first two of the pulse waves do not satisfy the predetermined condition, when the pulse wave interval of second two of the pulse waves, which are successively detected at a same cuff pressure, is within the predetermined range, and the waveform information of the second two of the pulse waves approximately coincide with each other, the determining unit may determine that an average of the amplitudes of the second two of the pulse waves is to be used for calculating the blood pressure.

The change trend calculating unit may calculate the change trend of the amplitudes as a slope of an envelope which is tangential to the amplitudes.

According to the invention, there is also provided a method of measuring a blood pressure in which pulse waves are successively detected in a step of gradually changing a cuff pressure adapted to press an artery, the method, wherein, when first two of the pulse waves, which are successively detected at different cuff pressures, satisfy a predetermined condition: that a magnitude relationship between amplitudes of the first two of the pulse waves is consistent with a change trend of the amplitudes; that a pulse wave interval between the first two of the pulse waves is within a predetermined range; and that waveform information of the first two of the pulse waves approximately coincide with each other, the amplitude of latter one of the first two of the pulse waves is to be used for calculating the blood pressure value.

In a case where the first two of the pulse waves do not satisfy the predetermined condition, when a pulse wave interval of second two of the pulse waves, which are successively detected at a same cuff pressure, is within the predetermined range, and waveform information of the second two of the pulse waves approximately coincide with each other, an average of the amplitudes of the second two of the pulse waves may be to be used for calculating the blood pressure.

DETAILED DESCRIPTION OF EMBODIMENTS

Hereinafter, an embodiment of the blood pressure measuring apparatus of the invention will be described with reference to the accompanying drawings.

Embodiment

Figure 1:
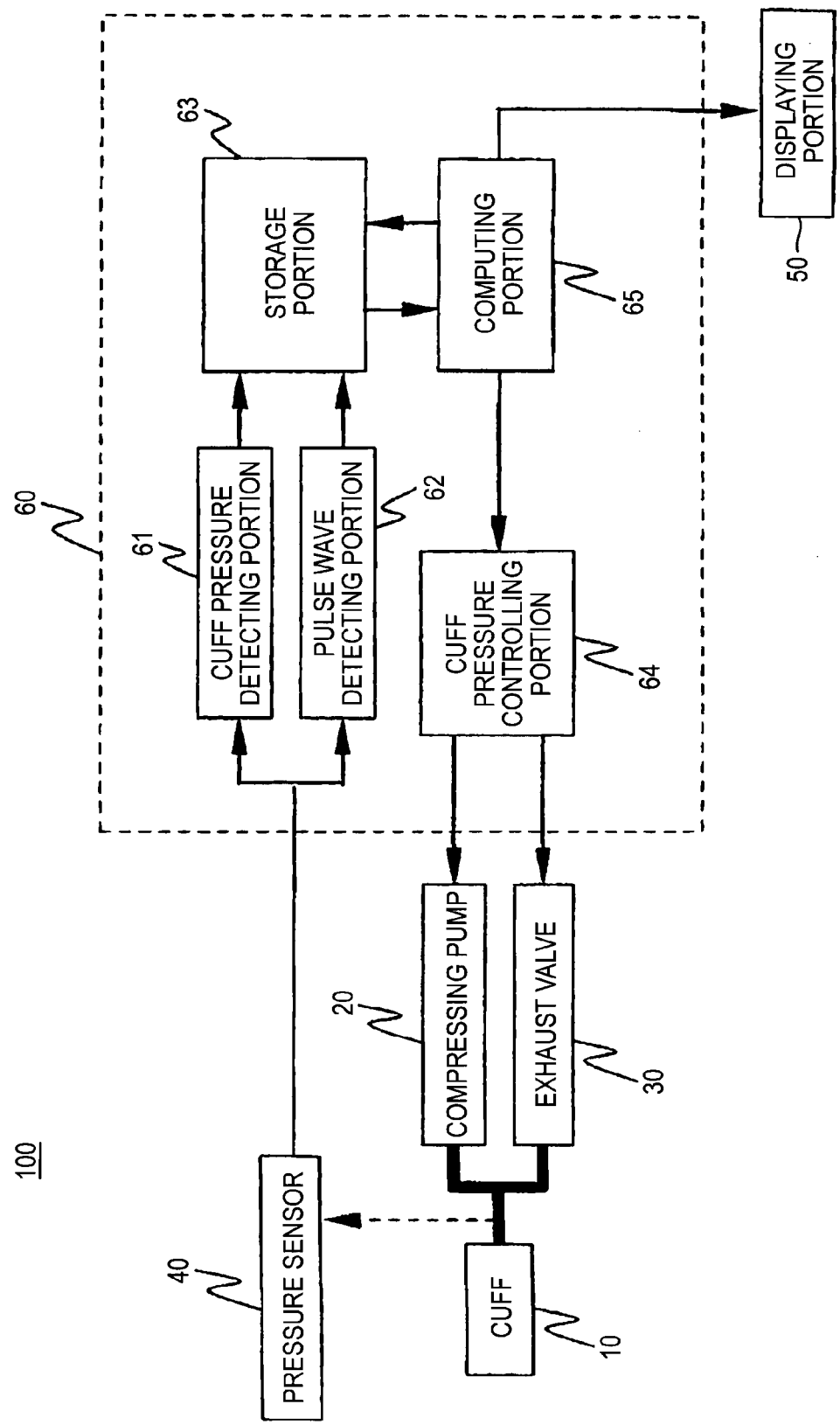
FIG. 1 is a block diagram illustrating a blood pressure measuring apparatus of an embodiment of the invention.
Figure 2:
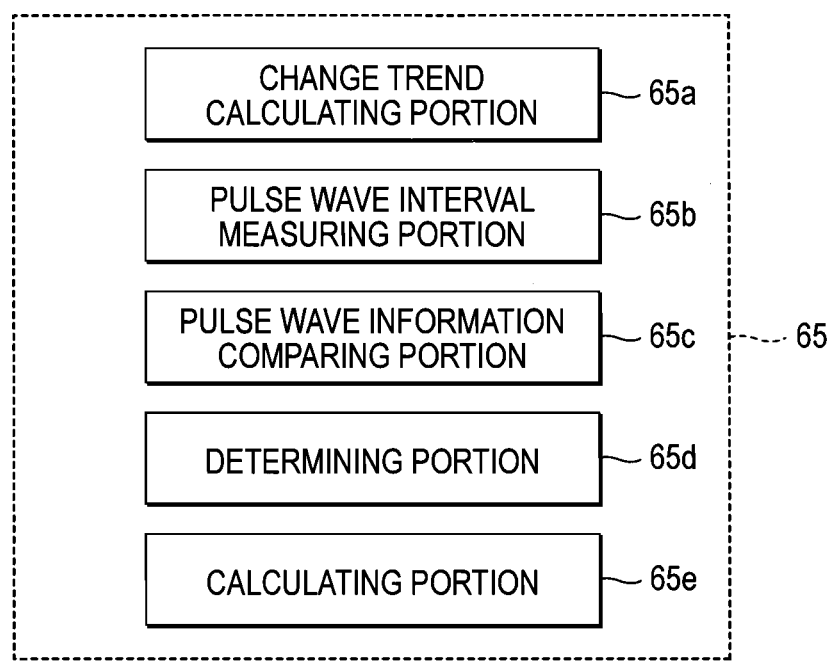
FIG. 2 is a block diagram illustrating a computing portion of the blood pressure measuring apparatus shown in FIG. 1.
Figure 3:
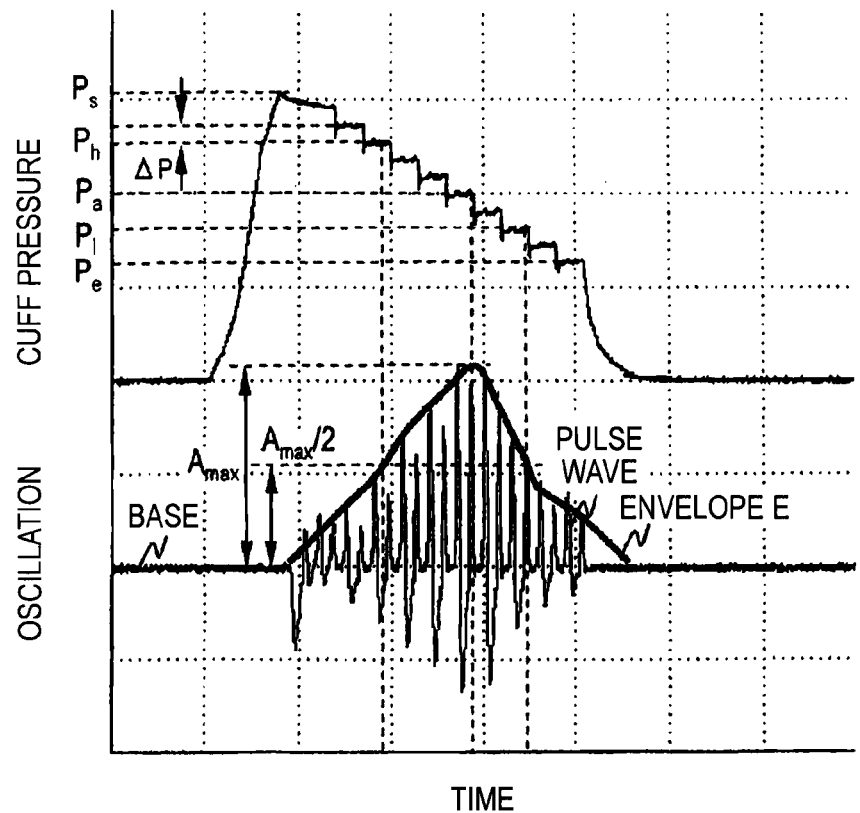
FIG. 3 is a waveform chart showing a relationship between a cuff pressure and oscillation.
Figure 4:
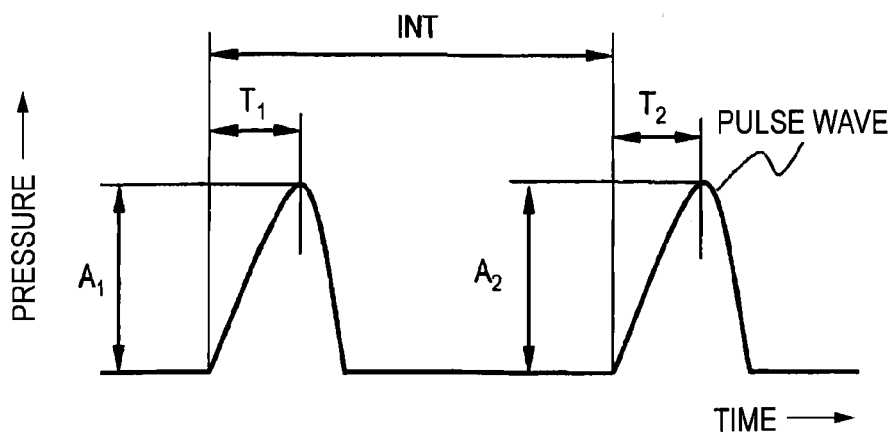
FIG. 4 is a diagram showing two successive pulse waves.

FIG. 1 is a schematic block diagram illustrating a blood pressure measuring apparatus of the embodiment of the invention, FIG. 2 is a block diagram illustrating a computing portion of the blood pressure measuring apparatus shown in FIG. 1, FIG. 3 is a waveform chart showing a relationship between a cuff pressure and pulse wave oscillation (hereafter, referred to as oscillation), and FIG. 4 is a diagram which shows two successive pulse waves, and in which the ordinate indicates the pressure, and the abscissa indicates the time.

In the case where it is determined that pulse waves are not affected by artifacts, the blood pressure measuring apparatus of the embodiment calculates the blood pressure value by using one pulse wave with respect to a specific cuff pressure. In the specification, all of the maximal blood pressure value, mean blood pressure value, and minimal blood pressure value are generally referred to as the blood pressure value.

As shown in FIG. 1, the blood pressure measuring apparatus 100 of the embodiment has a cuff 10, a compressing pump 20, an exhaust valve 30, a pressure sensor 40, a displaying portion 50, and a controlling portion 60.

The cuff 10 is to be wrapped around the upper arm or the like of the subject to press an artery. More specifically, a bag made of, for example, rubber is incorporated in the cuff 10, and, when air is supplied from the outside, the bag is inflated to press an artery of the subject.

The compressing pump 20 supplies air into the bag which is incorporated in the cuff 10. The exhaust valve 30 discharges the air accumulated in the cuff 10, to the outside. The compressing pump 20 and the exhaust valve 30 are controlled by the controlling portion 60 so as to cause the air pressure in the cuff 10 to have an adequate value.

The pressure sensor 40 detects the cuff pressure, also pulse waves from the artery of the subject, and outputs the detected pressure and pulse waves as an electrical signal. More specifically, the pressure sensor 40 has a semiconductor pressure sensor or the like, detects the air pressure in the cuff 10 and also oscillation of the artery of the subject, and outputs the detected pressure and oscillation as a pressure signal.

The displaying portion 50 displays the measured blood pressure value. More specifically, the displaying portion 50 includes, for example, a liquid crystal display panel, and displays the measured maximal, minimal, and mean blood pressure values, the pulse rate, and the like on the screen.

The controlling portion 60 controls the compressing pump 20 and the exhaust valve 30, calculates the blood pressure value based on the pressure signal supplied from the pressure sensor 40, and outputs the calculation result to the displaying portion 50. More specifically, the controlling portion 60 has a cuff pressure detecting portion 61, a pulse wave detecting portion 62, a storage portion 63, a cuff pressure controlling portion 64, and a computing portion 65.

The cuff pressure detecting portion 61 produces a cuff pressure signal based on the pressure signal supplied from the pressure sensor 40. More specifically, the cuff pressure detecting portion 61 has, for example, an amplifying circuit and an A/D converter, and the pressure signal supplied into the amplifying circuit is amplified to a predetermined voltage level, converted into a digital signal by the A/D converter, and then output as the cuff pressure signal to the storage portion 63.

The pulse wave detecting portion 62 produces a pulse wave signal based on the pressure signal supplied from the pressure sensor 40, to function as a pulse wave detecting unit. More specifically, the pulse wave detecting portion 62 has, for example, an amplifying circuit, a bandpass filter, and an A/D converter, and the pressure signal supplied to the amplifying circuit is amplified to a predetermined voltage level. A desired frequency band of the signal is extracted by the bandpass filter, converted into a digital signal by the A/D converter, and then output as the pulse wave signal to the storage portion 63.

The storage portion 63 stores various kinds of detection information and calculation results, and functions as a waveform information storage unit. More specifically, the storage portion 63 includes, for example, a RAM, and, as detection information, sequentially stores the cuff pressure $P_c$ of the cuff pressure signal produced by the cuff pressure detecting portion 61, and pulse wave information of the pulse wave signal produced by the pulse wave detecting portion 62. The pulse wave information of the pulse wave signal can include the amplitude A of a pulse wave, a time period which is required for a pulse wave to rise from a reference level to the amplitude A (hereinafter, the time period is referred to as the rising time T), a pulse wave interval INT, and the like. The storage portion 63 also stores a reference pulse wave interval INTr which will be described later, and an amplitude $A_{cn}$ and cuff pressure $P_{cn}$ which are to be used in calculation of the blood pressure value. The storage portion 63 further includes, for example, a ROM which stores a program indicating the blood pressure measurement procedure, various parameters for measuring the blood pressure, and the like.

The cuff pressure controlling portion 64 controls the air pressure in the cuff 10 through the compressing pump 20 and the exhaust valve 30. More specifically, when the blood pressure measurement is started, the cuff pressure controlling portion 64 receives instructions from the computing portion 65, and instructs the compressing pump 20 to perform a compressing operation so that the pressure of the cuff 10 rapidly reaches a starting pressure $P_s$. For example, the starting pressure $P_s$ has a value which is higher by a predetermined value than an expected maximal blood pressure value. As a result, the artery of the subject is pressed by a pressure which is higher by a predetermined pressure than the expected maximal blood pressure. Then, the cuff pressure controlling portion 64 receives instructions from the computing portion 65, and instructs the exhaust valve 30 to exhaust the air in the cuff 10 by a step of a predetermined amount, in order to gradually reduce the cuff pressure. As a result, as shown in FIG. 3, the cuff pressure is steeply raised to the starting pressure $P_s$, and then gradually reduced in a stepwise manner by a step of $\Delta P$. When the cuff pressure reaches an ending pressure $P_e$, the cuff pressure controlling portion 64 receives instructions from the computing portion 65, and instructs the exhaust valve 30 to exhaust the air in the cuff 10 so that the air pressure rapidly reaches the atmospheric pressure.

The computing portion 65 calculates the blood pressure value, and outputs the value to the displaying portion 50. More specifically, the computing portion 65 includes a CPU, issues instructions to the cuff pressure controlling portion 64 in accordance with the program which is stored in the ROM of the storage portion 63, and which indicates the blood pressure measurement procedure, and, based on the amplitude $A_{cn}$ and cuff pressure $P_{cn}$ which are registered in the storage portion 63, calculates the maximal, minimal, and mean blood pressure values and the pulse rate. The calculated values and number are output to the displaying portion 50. A specific step of calculating the blood pressure value in the computing portion 65 will be described later.

In the embodiment, in the relationship between the cuff pressure and oscillation which are shown in FIG. 3, the maximal, minimal, and mean blood pressure values are defined in the following manner. As shown in FIG. 3, when the blood pressure measurement is started, the cuff pressure is steeply raised to the starting pressure $P_s$, and then gradually reduced in a stepwise manner by the step of $\Delta P$, and, in accordance with the reduction of the cuff pressure, the amplitude A of the pulse wave signal is raised to reach the maximum, value $A_{max}$, and then reduced. In the embodiment, the cuff pressure at the timing when the maximum value $A_{max}$ of the amplitude of the pulse wave signal is obtained is referred as the mean blood pressure $P_a$, that at the timing when the amplitude that is ½ of the maximum value $A_{max}$ is obtained, and higher than the mean blood pressure $P_a$ is referred as the maximal blood pressure $P_h$, and that at the timing when the amplitude that is ½ of the maximum value $A_{max}$ is obtained, and lower than the mean blood pressure $P_a$ is referred as the minimal blood pressure $P_1$. In the embodiment, as shown in FIG. 3, the amplitude A of the pulse wave is defined as the height of the peak of the pulse wave signal which is measured with respect to the base.

Next, the function of the computing portion 65 in the step of calculating the blood pressure value will be described with reference to FIGS. 2 to 4. As shown in FIG. 2, the computing portion 65 has a change trend calculating portion 65a, a pulse wave interval measuring portion 65b, a pulse wave information comparing portion 65c, a determining portion 65d, and a calculating portion 65e.

The change trend calculating portion 65a functions as a change trend calculating unit which calculates the change trend of the pulse wave amplitudes that is to be used in the calculation of the blood pressure value. More specifically, the change trend calculating portion 65a calculates the change trend of the pulse wave amplitudes based on a plurality of pulse wave amplitudes $A_{cn}$ which are registered in the storage portion 63, and which are to be used in the calculation of the blood pressure value. By using a plurality of latest amplitudes $A_{cn}$ which are registered, for example, the change trend of the amplitudes is calculated as the slope of an envelope E which is tangential to the amplitudes. The slope of the envelope E is indicated as $\alpha$. When $\alpha>0$, the change trend $\alpha$ of the amplitudes $A_{cn}$ has an increasing tendency, and, when $\alpha<0$, the change trend $\alpha$ of the amplitudes $A_{cn}$ has a decreasing tendency.

The pulse wave interval measuring portion 65b functions as a pulse wave interval measuring unit which measures a pulse wave interval of two successive pulse waves. The pulse waves shown in FIG. 4 are waves in which pressure changes in a blood vessel due to contraction and expansion of the heart are transmitted to the blood vessel, and include a volume pulse wave (plethysmogram) and a pressure pulse wave. In the embodiment, a pressure pulse wave is detected. As shown in FIG. 4, the amplitudes of two successive pulse waves are defined as $A_1$, $A_2$, respectively, the rising times are defined as $T_1$, $T_2$, respectively, and the interval between the pulse waves is defined as the pulse wave interval INT. The pulse wave interval measuring portion 65b measures at a specific cuff pressure the interval of two successive pulse waves, i.e., the interval between a detected pulse wave and the pulse wave which is immediately previous to the detected pulse wave, and outputs a result of the measurement. More specifically, the pulse wave interval measuring portion 65b includes, for example, a counter which operates at a specific frequency. With respect to two successive pulse waves which are input to the storage portion 63, the counter measure the time period from the rising of the first pulse wave to that of the second pulse wave. A result of the measurement is output to the storage portion 63.

The pulse wave information comparing portion 65c functions as a waveform information comparing unit which compares sets of waveform information of two successive pulse waves with each other. More specifically, the pulse wave information comparing portion 65c compares waveform information of the pulse wave which is latter one of the successively detected pulse waves with that of the pulse wave which is immediately previous to the latter pulse wave, and supplies a result of the comparison to the storage portion 63. As described above, waveform information of a pulse wave includes the amplitude A, rising time T, and the like of the pulse wave. In the comparison between amplitudes of pulse waves, the magnitude relationship between the amplitudes $A_1$, $A_2$ of two successive pulse waves is output. The magnitude relationship includes also information indicative of an increasing tendency (positive) or a decreasing tendency (negative) as the change trend of the amplitudes $A_1$, $A_2$. Based on the amplitudes $A_1$, $A_2$ and rising times $T_1$, $T_2$ of the two successive pulse waves, the waveform shapes are compared with each other, and a result of the comparison is output. As the comparison result, for example, the difference $\Delta A$ between the amplitudes of the two successive pulse waves, and the difference $\Delta T$ between the rising times $T_1$, $T_2$ are output.

The determining portion 65d functions as a determining unit which determines whether a detected pulse wave is to be used for calculating the blood pressure value or not. More specifically, the determining portion 65d determines whether a detected pulse wave is to be used in calculation of the blood pressure value or not, based on the change trend of the amplitudes, the measurement result of the pulse wave interval, and the comparison result of the pulse wave information, and registers the amplitude $A_{cn}$ and the cuff pressure $P_{cn}$ at that time in the storage portion 63.

The calculating portion 65e calculates the blood pressure value based on the amplitudes $A_{cn}$ and cuff pressures $P_{cn}$ which are registered, and outputs the calculated values to the displaying portion 50. More specifically, the calculating portion 65e calculates the mean blood pressure $P_a$, the maximal blood pressure $P_h$, and the minimal blood pressure $P_1$ as blood pressure values, based on a plurality of amplitudes $A_{cn}$ which are registered in the storage portion 63 on the basis of the judgment result of the determining portion 65d, and cuff pressures $P_{cn}$ corresponding to the amplitudes, and outputs the calculated values to the displaying portion 50.

Hereinafter, a blood pressure measuring method of the embodiment will be described with reference to FIG. 5. In the blood pressure measuring method of the embodiment, if it is determined that pulse waves are not affected by artifacts, the blood pressure is calculated by using one pulse wave with respect to a specific cuff pressure $P_c$.

Figure 5:
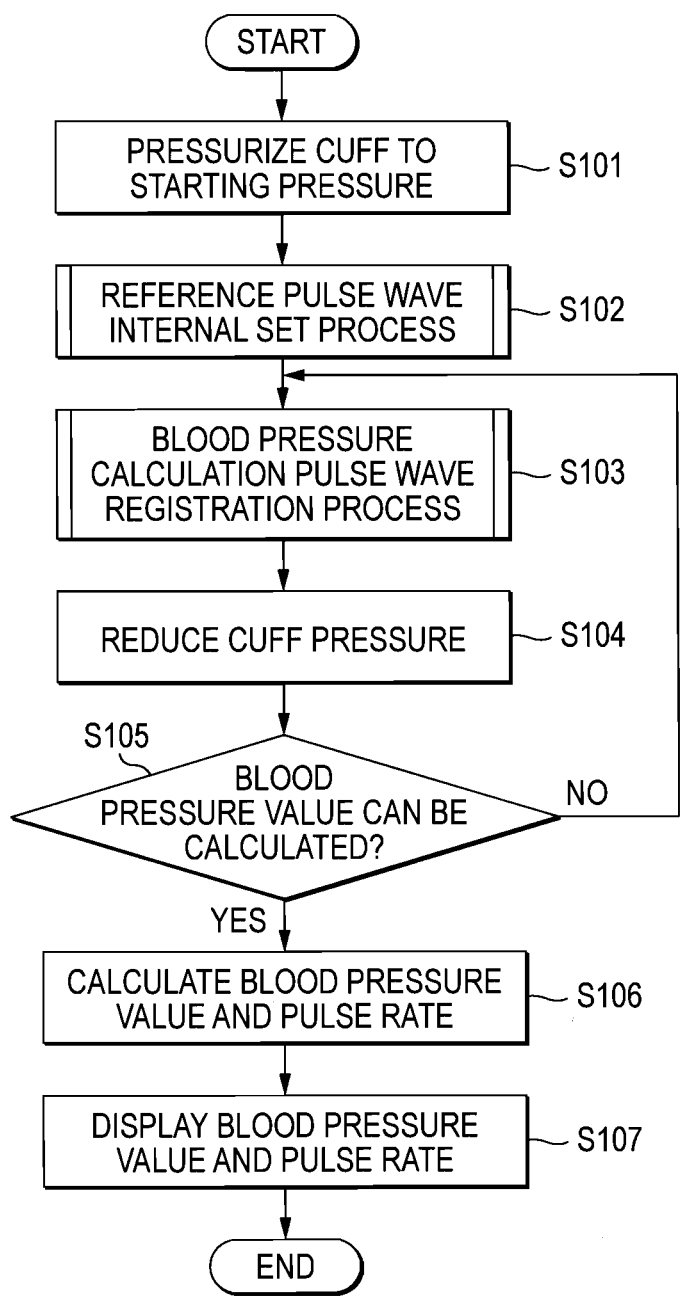
FIG. 5 is a flowchart illustrating a process of a blood pressure measuring method of the embodiment of the invention.

FIG. 5 is a flowchart illustrating a process of the blood pressure measuring method of the embodiment. Hereinafter, a process performed from the pressing by the cuff after the start of the blood pressure measurement to the displaying of the blood pressure value at the timing when the blood pressure measurement is ended will be described.

As shown in FIG. 5, first, the cuff 10 is pressurized to the starting pressure $P_s$ (step S101). More specifically, the cuff pressure controlling portion 64 controls the compressing pump 20 to feed air into the cuff 10, whereby the cuff is pressurized to the starting pressure $P_s$ which is higher by the predetermined value than the expected maximal blood pressure value of the subject. The expected maximal blood pressure value may be set, for example, based on the maximal blood pressure value which is obtained in the last measurement.

Next, a reference pulse wave interval set process is executed (step S102). In the reference pulse wave interval set process, the reference pulse wave interval INTr is registered. A specific function of the reference pulse wave interval set process will be described later.

Next, a blood pressure calculation pulse wave registration process is executed (step S103). In the blood pressure calculation pulse wave registration process, the amplitude $A_{cn}$ and cuff pressure $P_{cn}$ which are used in the calculation of the blood pressure value are registered by using the detected pulse waves. A specific function of the blood pressure calculation pulse wave registration process will be described later.

Next, the cuff pressure is reduced (step S104). More specifically, the pressure in the cuff 10 is reduced by a predetermined minute pressure $\Delta P$. For example, the minute pressure $\Delta P$ is about 3 to 10 mmHg.

Then, it is determined whether the blood pressure value can be calculated or not (step S105). More specifically, in the case where the envelope E calculated from the plurality of pulse wave amplitudes $A_{cn}$ which are registered in the blood pressure calculation pulse wave registration process monotonically increases and then monotonically decreases, and the lastly registered pulse wave amplitude value is smaller than ½ of the maximum value $A_{max}$, it is determined that the blood pressure value can be calculated. In the other case, it is determined that the blood pressure value cannot be calculated. If it is determined that the blood pressure value cannot be calculated (step S105: NO), the process returns to the blood pressure calculation pulse wave registration process (step S103).

By contrast, if it is determined that the blood pressure value can be calculated (step S105: YES), the blood pressure value and the pulse rate are calculated (step S106). More specifically, the cuff pressure controlling portion 64 controls the exhaust valve 30 to exhaust the air in the cuff 10 to the outside, whereby the cuff pressure is rapidly reduced from the ending pressure $P_e$ to the atmospheric pressure, and the calculating portion 65e of the computing portion 65 calculates the blood pressure value and the pulse rate based on the pluralities of registered pulse wave amplitudes $A_{cn}$ and cuff pressures $P_{cn}$. In the embodiment, the cuff pressure at the timing when the maximum value $A_{max}$ of the pulse wave signal is obtained is referred as the mean blood pressure $P_a$, that at the timing when the amplitude that is ½ of the maximum value $A_{max}$ is obtained, and higher than the mean blood pressure $P_a$ is referred as the maximal blood pressure $P_h$, and that at the timing when the amplitude that is ½ of the maximum value $A_{max}$ is obtained, and lower than the mean blood pressure $P_a$ is referred as the minimal blood pressure $P_l$. The pulse rate is calculated based on the average value of the pulse wave interval INT.

Next, the blood pressure value and the pulse rate are displayed on the displaying portion 50 (step S107). As a result, the operator can check the maximal, minimal, and mean blood pressures and pulse rate which are measured, on the liquid crystal display panel of the displaying portion 50.

Figure 6:
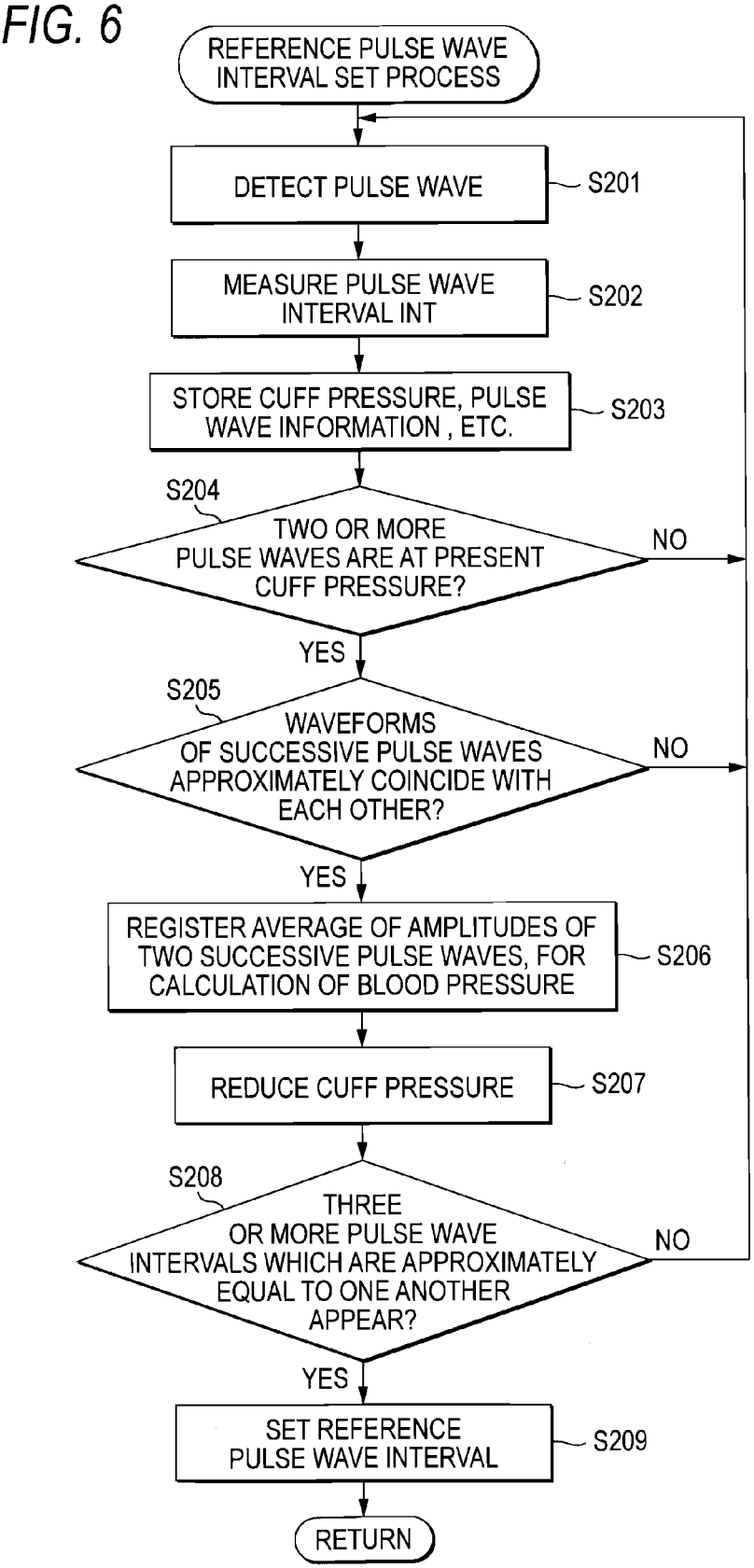
FIG. 6 is a flowchart illustrating a reference pulse wave interval set process in the process shown in FIG. 5.

Next, the reference pulse wave interval set process will be described with reference to FIG. 6. FIG. 6 is a flowchart illustrating the reference pulse wave interval set process in the process shown in FIG. 5.

The reference pulse wave interval set process is a process of setting the reference pulse wave interval INTr. The reference pulse wave interval INTr is used in a comparison where the most frequently appearing pulse wave interval among pulse wave intervals INT of two-successive pulse intervals is used as a reference, and the reference pulse wave interval is compared with subsequently measured pulse wave intervals INT. In the case where three pulse wave intervals which are approximately equal to one another appear, for example, the reference pulse wave interval INTr is calculated and set based on the pulse wave intervals. The method of calculating the reference pulse wave interval INTr will be described below.

As shown in FIG. 6, first, the pulse wave of the artery is detected (step S201). More specifically, the pulse wave signal and the cuff pressure signal are produced based on the pressure signal supplied from the pressure sensor 40.

Next, the pulse wave interval INT is measured (step S202). More specifically, the pulse wave interval INT of two pulse waves which are successively detected is measured.

Next, the cuff pressure, the pulse wave information, and the like are stored (step S203). More specifically, the cuff pressure $P_c$ is extracted from the cuff pressure signal which is produced in step S201, the pulse wave information is extracted from the produced pulse wave signal, and the cuff pressure and the pulse wave information are stored in the storage portion 63. Also the pulse wave interval INT which is obtained in step S202 is stored in the storage portion 63.

Next, it is determined whether two or more pulse waves are at the present cuff pressure $P_c$ or not (step S204). If the first pulse wave (step S204: NO), the process returns to step S201 to detect the pulse wave.

By contrast, if two or more pulse waves are at the present cuff pressure $P_c$ (step S204: YES), it is determined whether two successive pulse waves approximately coincide with each other or not (step S205). If the two pulse waves approximately coincide with each other (step S205: YES), the average of the amplitudes $A_1$, $A_2$ of the two successive pulse waves is determined to be used as the amplitude $A_{cn}$ which is to be used in the calculation of the blood pressure value, and registered in the storage portion 63 (step S206). More specifically, if the difference between the amplitudes $A_1$, $A_2$ of the two successive pulse waves is within a range of, for example, ±25% of the amplitude $A_1$, and that between the rising times $T_1$, $T_2$ is within a range of, for example, ±30% of the rising time $T_1$, it is determined that the waveforms of the two successive pulse waves coincide with each other. By contrast, if two successive pulse waves which approximately coincide with each other are not detected (step S205: NO), the process returns to step S201 to detect the pulse wave.

Next, the cuff pressure is reduced (step S207). More specifically, the cuff pressure is reduced by the predetermined minute pressure $\Delta P$.

Next, it is determined whether three or more pulse wave intervals which are approximately equal to one another appear or not (step S208). If three or more pulse wave intervals which are approximately equal to one another appear (step S208: YES), the reference pulse wave interval INTr is calculated and set based on the pulse wave intervals (step S209). More specifically, in a range of values which can be possessed by the measured pulse wave intervals INT, the pulse wave intervals INT are sequentially classified into a plurality of classes in accordance with a value, and the frequency of occurrence is calculated for each of the classes. A representative value of a class in which the frequency of occurrence is three or more is set as the reference pulse wave interval INTr in the storage portion 63. When the magnitude relationship of the frequencies of occurrence of the classes is changed during the measurement, the reference pulse wave interval INTr is reset to a representative value of a class having the largest frequency of occurrence. The threshold of the pulse wave intervals INT with respect to the frequency of occurrence is not limited to three, and may be adequately changed. By contrast, if three or more pulse wave intervals which are approximately equal to one another do not appear (step S208: NO), the process returns to step S201 to detect the pulse wave.

Figure 7:
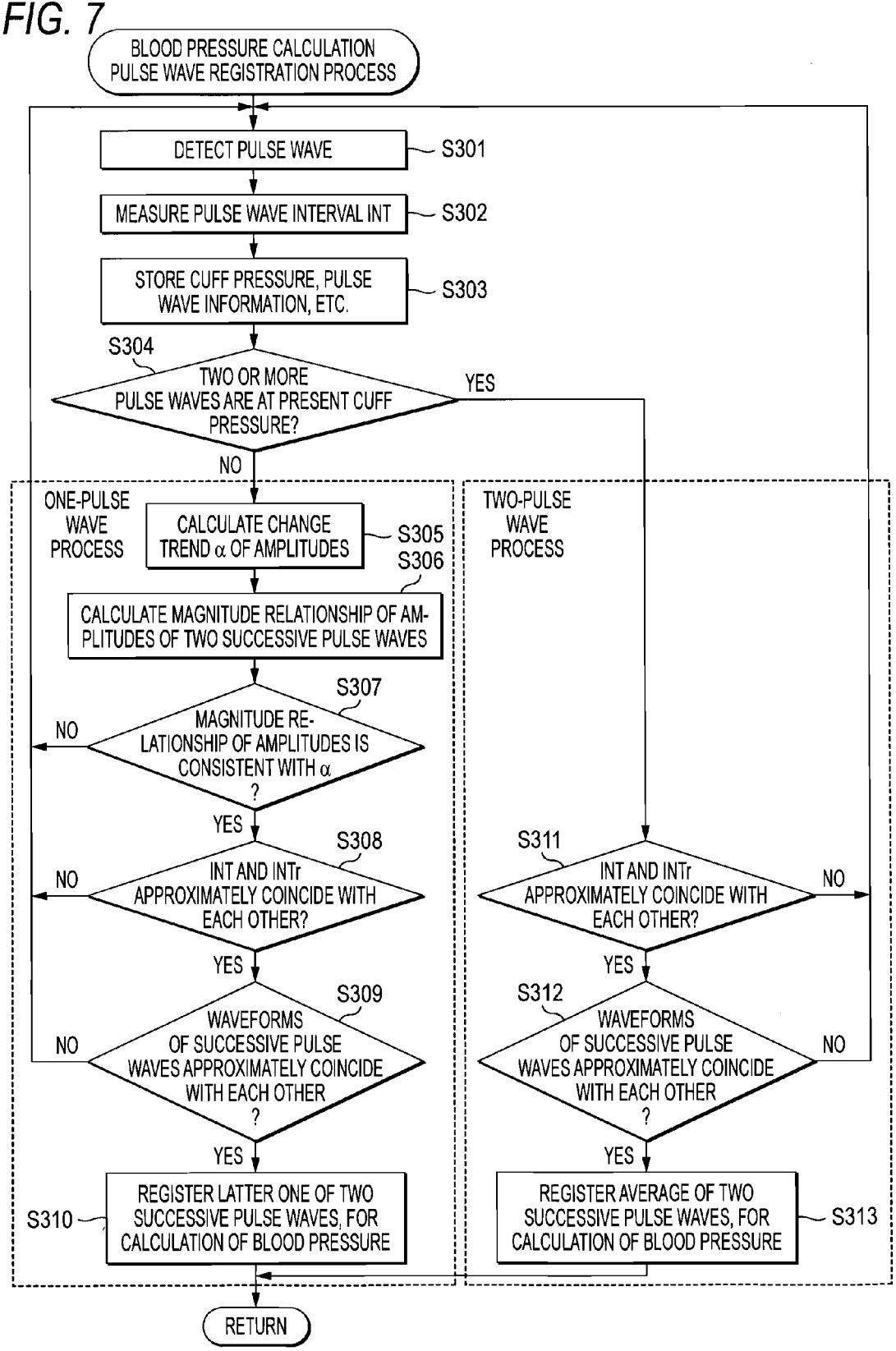
FIG. 7 is a flowchart illustrating a blood pressure calculation pulse wave registration process in the process shown in FIG. 5.

Next, the blood pressure calculation pulse wave registration process will be described with reference to FIG. 7. FIG. 7 is a flowchart illustrating the blood pressure calculation pulse wave registration process in the process shown in FIG. 5.

In the blood pressure calculation pulse wave registration process in the embodiment, in the case where two successive pulse waves are consistent with each other in the step of gradually reducing the cuff pressure from the starting pressure $P_s$ to the ending pressure $P_e$ in a stepwise manner, the amplitude $A_2$ of the latter one of the two pulse waves is registered as the amplitude $A_{cn}$ of the pulse wave which is to be used in the calculation of the blood pressure value. By contrast, in the case where two successive pulse waves are not consistent with each other, the average of the amplitudes $A_1$, $A_2$ of the two successive pulse waves is registered as the amplitude $A_{cn}$ which is to be used in the calculation of the blood pressure value. For the sake of convenience in the following description, the blood pressure calculation pulse wave registration process will be described separately for both a one-pulse wave process and a two-pulse wave process.

As shown in FIG. 7, first, the pulse wave of the artery is detected (step S301). More specifically, the pulse wave signal and the cuff pressure signal are produced based on the pressure signal supplied from the pressure sensor 40.

Next, the pulse wave interval INT is measured (step S302). More specifically, the pulse wave interval INT of two pulse waves which are successively detected is measured.

Next, the cuff pressure, the pulse wave information, and the like are stored (step S303). More specifically, the cuff pressure $P_c$ is extracted from the cuff pressure signal which is produced in step S301, the pulse wave information is extracted from the produced pulse wave signal, and the cuff pressure and the pulse wave information are stored in the storage portion 63. Also the pulse wave interval INT which is obtained in step S302 is stored in the storage portion 63.

Next, it is determined whether two or more pulse waves are at the present cuff pressure $P_c$ or not (step S304). If two or more pulse waves are not at the present cuff pressure (step S304: NO), the one-pulse wave process is executed, and, if two or more pulse waves are at the present cuff pressure (step S304: YES), the two-pulse wave process is executed. Hereinafter, the one-pulse wave process is first described, and the two-pulse wave process is then described.

<One-Pulse Wave Process>

If the first pulse wave (step S304: NO), first, the change trend of the amplitudes is calculated (step S305). More specifically, the slope a of the envelope E is calculated based on the plurality of registered pulse wave amplitudes $A_{cn}$.

Next, the magnitude relationship of the amplitudes of two successive pulse waves is calculated (step S306). More specifically, the pulse wave information comparing portion 65c of the computing portion 65 compares the magnitude relationship between the amplitudes $A_1$, $A_2$ of two successive pulse waves which are respectively a pulse wave obtained before the reduction of the cuff pressure, and that obtained after the reduction of the cuff pressure, with each other, to calculate $\Delta A=(A_1-A_2)$.

Next, consistency between the magnitude relationship of the amplitudes and the change trend of the amplitudes is determined (step S307). More specifically, If $\alpha>0$ and $A_1<A_2$ or $\alpha<0$ and $A_1>A_2$, or $\alpha\cong0$ and $A_1\cong A_2$ are satisfied, i.e., if the product of $\alpha$ and $\Delta A$ is equal to or larger than 0 or $\alpha\cdot\Delta A\geq0$, it is determined that the change trend $\alpha$ of the amplitudes and the magnitude relationship of the amplitudes $A_1$, $A_2$ of two successive pulse waves are consistent with each other (step S307: YES). By contrast, if the above-described relationships are not satisfied, it is determined that consistency is not obtained (step S307: NO). In the case where it is determined that consistency is not obtained, the process returns to the detection of the pulse wave (step S301).

Next, it is determined whether the pulse wave interval INT and the reference pulse wave interval INTr approximately coincide with each other or not (step S308). More specifically, if the difference between the pulse wave interval INT and the reference pulse wave interval INTr is within a range of, for example, ±30% of the reference pulse wave interval INTr, it is determined that the intervals approximately coincide with each other. If the pulse wave interval INT and the reference pulse wave interval INTr do not coincide with each other (step S308: NO), the process returns to the detection of the pulse wave (step S301).

By contrast, if the pulse wave interval INT and the reference pulse wave interval INTr approximately coincide with each other (step S308: YES), sets of waveform information of two pulse waves which are successively detected are compared with each other (step S309). More specifically, if the difference between the amplitudes $A_1$, $A_2$ of the two successive pulse waves is within a range of, for example, ±25% of the amplitude $A_1$, and that between the rising times $T_1$, $T_2$ is within a range of, for example, ±30% of the rising time $T_1$, it is determined that the waveforms of the two successive pulse waves approximately coincide with each other. If the waveforms of the two successive pulse waves do not coincide with each other (step S309: NO), the process returns to the detection of the pulse wave (step S301).

By contrast, if the waveforms of the two successive pulse waves approximately coincide with each other (step S309: YES), the latter one of the two successive pulse waves is registered as a pulse wave for calculation of the blood pressure value (step S310). More specifically, the amplitude $A_2$ of the latter pulse wave which, in the two successive pulse waves, is the pulse wave that is at the present cuff pressure $P_{cn}$ and the cuff pressure $P_c$ at this time are registered as the values for calculation of the blood pressure value in the storage portion 63. Then, the process returns from the blood pressure calculation pulse wave registration process to the process shown in FIG. 5.

In the one-pulse wave process, in the case where, with respect to two pulse waves which are successively detected at different cuff pressures, the magnitude relationship between the amplitudes $A_1$, $A_2$ is consistent with the change trend $\alpha$ calculated by the change trend calculating portion 65a, the pulse wave interval INT is within the predetermined range, and sets of waveform information approximately coincide with each other, as described above, the determining portion 65d of the computing portion 65 determines that the amplitude $A_2$ of the later detected one of two pulse waves which are successively detected is to be used in the calculation of the blood pressure value, and registers the amplitude in the storage portion 63. In the other case, it is determined that the amplitude of the later detected one of two pulse waves which are successively detected is not to be used as it is in the calculation of the blood pressure value, and the process is transferred to the two-pulse wave process which will be described below.

<Two-Pulse Wave Process>

Next, the case where the blood pressure calculation pulse wave registration process is performed based on two pulse waves will be described. If it is determined in step S304 above that two or more pulse waves are at the present cuff pressure $P_c$ (step S304: YES), it is determined whether the pulse wave interval INT and the reference pulse wave interval INTr approximately coincide with each other or not (step S311). More specifically, if the difference between the pulse wave interval INT and the reference pulse wave interval INTr is within a range of, for example, ±30% of the reference pulse wave interval INTr, it is determined that the intervals coincide with each other. If the pulse wave interval INT and the reference pulse wave interval INTr do not coincide with each other (step S311: NO), the process returns to the detection of the pulse wave (step S301).

By contrast, if the pulse wave interval INT and the reference pulse wave interval INTr approximately coincide with each other (step S311: YES), sets of waveform information of two pulse waves which are successively detected are compared with each other (step S312). More specifically, if the difference between the amplitudes $A_1$, $A_2$ of the two successive pulse waves is within a range of, for example, ±25% of the amplitude $A_1$, and that between the rising times $T_1$, $T_2$ is within a range of, for example, ±30% of the rising time $T_1$, it is determined that the waveforms of the two successive pulse waves approximately coincide with each other. If the waveforms of the two successive pulse waves do not coincide with each other (step S312: NO), the process returns to the detection of the pulse wave (step S301).

By contrast, if the waveforms of the two successive pulse waves approximately coincide with each other (step S312: YES), the average of the two successive pulse waves is registered as the value for calculation of the blood pressure value (step S313). More specifically, the determining portion 65*d* of the computing portion 65 registers the average of the amplitudes $A_1$, $A_2$ of two pulse waves which are successively detected, and the cuff pressure $P_c$ are registered as the values for calculation of the blood pressure value in the storage portion 63. Then, the process returns from the blood pressure calculation pulse wave registration process to the process shown in FIG. 5.

In the two-pulse wave process, in the case where the pulse wave interval INT is within the predetermined range and sets of waveform information approximately coincide with each other, as described above, it is determined that the average of the amplitudes $A_1$, $A_2$ of two pulse waves which are successively detected is to be used in the calculation of the blood pressure value. In the case where the pulse wave interval INT and the reference pulse wave interval INTr do not coincide with each other, or in the case where the waveforms of the two successive pulse waves do not coincide with each other, the detection of the pulse wave is continued while maintaining the present cuff pressure $P_c$.

EXAMPLE

Figure 8:
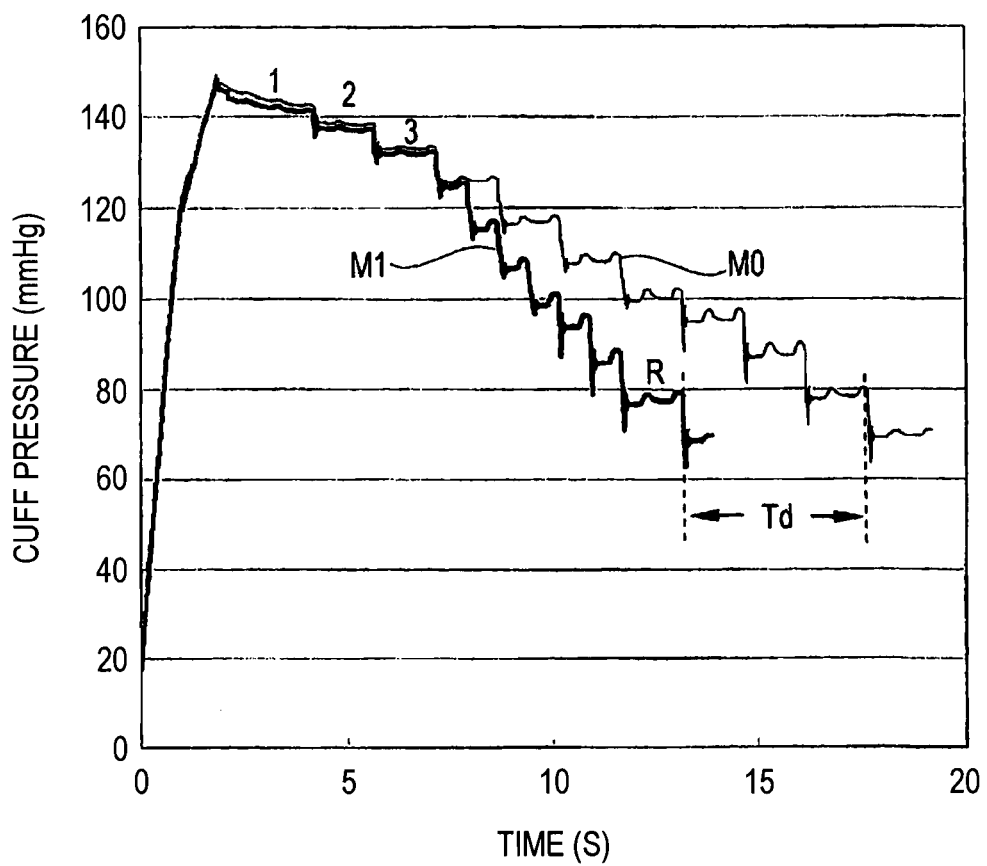
FIG. 8 is a view showing changes of cuff pressures in a blood pressure measurement by the blood pressure measuring apparatus shown in FIG. 1, and in a related-art blood pressure measurement.

Next, an example of the blood pressure measurement which is performed by the blood pressure measuring apparatus of the embodiment will be described with reference to FIG. 8. FIG. 8 is a view showing changes of cuff pressures in the blood pressure measurement by the blood pressure measuring apparatus shown in FIG. 1, and in the related-art blood pressure measurement. The waveform M1 shows the change of the cuff pressure in the blood pressure measurement in the embodiment, and the waveform M0 shows the change of the cuff pressure in the related-art blood pressure measurement which is a comparative example.

As shown in FIG. 8, in the related-art blood pressure measurement, the detection is always conducted by using two pulse waves in the blood pressure calculation pulse wave registration process. In the blood pressure measurement in the embodiment, by contrast, the detection is conducted by using one pulse wave except the initial three detection processes (the reference pulse wave interval set process) indicated by the numerals 1 to 3, and the last detection process indicated by R. The detection processes indicated by the numerals 1 to 3 correspond to the process of setting the reference pulse wave interval INTr in the initialization process, and the followings are shown. It is determined that, in the detection process indicated by R, a detected pulse wave is affected by artifacts, and the process is transferred from the one-pulse wave process to the two-pulse wave process. In the blood pressure measurement in the embodiment, the measurement can be completed earlier by Td than the related-art blood pressure measurement.

As described above, the above-described embodiment attains the following effects.

According to an aspect of the invention, in the case where it is determined that pulse waves are not affected by artifacts, the blood pressure values is calculated by using one pulse wave with respect to a specific cuff pressure, and hence the time period which is required for the blood pressure measurement can be significantly shortened.

According to an aspect of the invention, as conditions for determining that pulse waves are not affected by artifacts, the following conditions are set: that, with respect to latest two successive pulse waves, the magnitude relationship between the amplitudes of the pulse waves is consistent with the change trend of the latest amplitudes which is registered for calculating the blood pressure value; that the interval of the pulse waves is within the predetermined range; and that sets of waveform information of the pulse waves approximately coincide with each other. Therefore, erroneous detection of a pulse wave can be significantly reduced.

According to an aspect of the invention, usually, the blood pressure value is calculated by using one pulse wave, so that the time period which is required for the blood pressure measurement is shortened, and, even in the case where it is determined that pulse waves are affected by artifacts, the blood pressure value is calculated by using the average of two pulse waves. Therefore, the blood pressure value can be surely calculated.

In the embodiment, the blood pressure measuring apparatus and method of the invention have been described. In the invention, however, it is a matter of course that those skilled in the art can adequately perform addition, modification, and deletion within the scope of the technical concept of the invention.

In the above-described embodiment, for example, the amplitude which is to be used in the calculation of the blood pressure value is not obtained until two successive pulse waves satisfy the predetermined conditions. In view of safety and convenience in measurement of the blood pressure, however, the blood pressure measuring apparatus may include a mechanism which interrupts or terminates the measurement process depending on the measurement situation.

In the embodiment, for the sake of convenience, the reference pulse wave interval set process and the blood pressure calculation pulse wave registration process have been described with reference to the independent flowcharts. However, the reference pulse wave interval set process may be incorporated into the blood pressure calculation pulse wave registration process.

In the embodiment described above, the computing portion includes the CPU, and is controlled by the program which is stored in the ROM of the storage portion, and which indicates the blood pressure measurement procedure, so as to perform the blood pressure measurement process. However, the blood pressure measuring apparatus of the invention is not limited to the above-described configuration, and the blood pressure measurement process may be performed by controlling the computing portion by hardware.

In the embodiment described above, the blood pressure value is calculated while setting: the cuff pressure at the timing when the maximum value $A_{max}$ of the pulse wave signal is obtained, as the mean blood pressure $P_a$; that at the timing when the amplitude that is ½ of the maximum value $A_{max}$ is obtained, and higher than the mean blood pressure $P_a$, as the maximal blood pressure $P_h$; and that at the timing when the amplitude that is ½ of the maximum value $A_{max}$ is obtained, and lower than the mean blood pressure $P_a$, as the minimal blood pressure $P_1$. However, the maximal blood pressure $P_h$ and the minimal blood pressure $P_1$ may be calculated based on another definition.

What is claimed is:

1. A method of measuring a blood pressure in which pulse waves are successively detected in a step of gradually changing a cuff pressure adapted to press an artery comprising:
   a) inflating a cuff;
   b) sensing, via a pressure sensor, cuff pressure and pulse waves of the artery;
   c) determining, with a processor, whether two or more pulse waves are at the present cuff pressure;
   d) determining, with the processor, whether first two of the pulse waves, which are successively detected at different cuff pressures, satisfy predetermined conditions:
      that a magnitude relationship between amplitudes of the first two of the pulse waves is consistent with a change trend of the amplitudes; and
      that a pulse wave interval between the first two of the pulse waves is within a predetermined range; and
      that waveform information of the first two of the pulse waves approximately coincide with each other;
   e) selecting, with the processor, the latter of first two of the pulse waves in response to the predetermined conditions being satisfied;
   f) determining, with the processor, whether blood pressure can be calculated, and repeating steps c), d), and e) if blood pressure cannot be calculated; and
   g) calculating the blood pressure with the processor when the predetermined conditions are satisfied with the amplitude of latter one of the first two of the pulse waves.

2. The method according to claim 1, further comprising:
   h) determining, with the processor, when two or more pulse waves are at the present cuff pressure, whether second predetermined conditions are satisfied:
      that a pulse wave interval of second two of the pulse waves, which are successively detected at a same cuff pressure, is within the predetermined range, and waveform information of the second two of the pulse waves approximately coincide with each other;
   i) determining, with the processor, whether blood pressure can be calculated, and repeating step c) and steps d) and e), or
      step h), if blood pressure cannot be calculated; and
   j) calculating the blood pressure with the processor when the second predetermined conditions are satisfied using an average of the amplitudes of the second two of the pulse waves.

3. The method according to claim 1, further comprising displaying the calculated blood pressure on a display.

* * * * *